(12) United States Patent  (10) Patent No.: US 8,089,424 B2
Huh  (45) Date of Patent: Jan. 3, 2012

(54) FUNCTIONAL DISPLAY TYPE ANTI-BLINDING DEVICE

(75) Inventor: Moon young Huh, Seoul (KR)

(73) Assignee: Otos Tech Co., Ltd. (KR)

( * ) Notice: Subject to any disclaimer, the term of this patent is extended or adjusted under 35 U.S.C. 154(b) by 341 days.

(21) Appl. No.: 12/549,986

(22) Filed: Aug. 28, 2009

(65) Prior Publication Data

US 2010/0090997 A1 Apr. 15, 2010

(30) Foreign Application Priority Data

Oct. 14, 2008 (KR) ........................ 10-2008-0100402

(51) Int. Cl.
*G09G 5/00* (2006.01)
(52) U.S. Cl. ........... 345/8; 345/7; 2/8.2; 349/13; 349/14
(58) Field of Classification Search .................. 345/7, 8; 349/13, 14; 2/8.2
See application file for complete search history.

(56) References Cited

U.S. PATENT DOCUMENTS

| | | | | |
|---|---|---|---|---|
| 5,571,258 A | * | 11/1996 | Pearson | ........................ 221/211 |
| 5,959,705 A | * | 9/1999 | Fergason | ........................ 349/14 |
| 6,067,129 A | * | 5/2000 | Fergason | ........................ 349/14 |
| 6,483,090 B1 | | 11/2002 | Bae | |
| 6,552,316 B1 | | 4/2003 | Bae | |
| 6,614,409 B1 | * | 9/2003 | Bae | ................................... 345/8 |
| 7,342,210 B2 | * | 3/2008 | Fergason | ..................... 250/206 |
| 7,470,880 B2 | | 12/2008 | Huh | |
| 7,564,014 B2 | | 7/2009 | Huh | |
| 2005/0007504 A1 | * | 1/2005 | Fergason | ........................ 349/14 |
| 2009/0094721 A1 | * | 4/2009 | Becker | ............................... 2/8.8 |

* cited by examiner

*Primary Examiner* — Adam R Giesy
(74) *Attorney, Agent, or Firm* — Cantor Colburn LLP

(57) ABSTRACT

Disclosed is a functional display type anti-blinding device having an anti-blinding plate for indication and control of a screen display condition and variation in light transmittance. The anti-blinding plate includes a filter to selectively filter light, a polarizer to polarize the filtered light, a shutter LCD having a variable light transmittance based on control of a light transmission control unit, a transparent dot-matrix LCD to indicate the screen display condition based on control of a display control unit, and a glass protector at the rear of the transparent dot-matrix LCD. The shutter LCD flickers several times to indicate an initial state and is turned off. The transparent dot-matrix LCD is turned on upon turn-off of the shutter LCD to indicate the screen display condition. The shutter LCD is turned on upon turn-off of the transparent dot-matrix LCD to transmit light based on preset light transmittance.

24 Claims, 6 Drawing Sheets

FUNCTIONAL DISPLAY TYPE ANTI-BLINDING DEVICE

This application claims priority to Korean Patent Application No. 10-2008-100402, filed on Oct. 13, 2008, and all the benefits accruing therefrom under 35 U.S.C §119, the contents of which in its entirety are hereby incorporated by reference.

BACKGROUND OF THE INVENTION

1. Field of the Invention

The present invention relates to a functional display type anti-blinding device, and more particularly, to a functional display type anti-blinding device having an anti-blinding plate, which may assure effective indication and control of a screen display condition as well as a variation in light transmittance and consequently, may assure the control of innovative displays.

2. Description of the Related Art

Generally, during a welding, cutting, or grinding operation, a welding mask is generally used to protect the operator's eyes from glare and various toxic substances. Recently, a variety of kinds of safe and convenient electronic welding masks have been developed and used.

FIG. 1 is a perspective view illustrating a conventional protective mask including an anti-blinding device.

As shown in FIG. 1, the protective mask 1, which is provided at a front surface thereof with the anti-blinding device 2, may reduce the illumination intensity of light directed to the operator's eyes using an anti-blinding plate 5. The anti-blinding plate 5 takes the form of a Liquid Crystal Display (LCD) included in the anti-blinding device 2.

Specifically, the anti-blinding device 2 further includes a photo-sensor unit 4, such as, e.g., a photodiode attached to a front surface thereof. The photo-sensor unit 4 is adapted to sense light emitted from a welding or cutting torch. As a control circuit mounted in the anti-blinding device 2 controls the anti-blinding plate 5 to be darkened based on the sensed result such that the illumination intensity of light passing through the anti-blinding plate 5 is reduced, the anti-blinding device 2 may serve to protect the eyes of the operator who wears the protective mask 1.

FIG. 2 is a view illustrating a user interface used to adjust shade, light detection sensitivity, and time delay of the conventional anti-blinding device.

Referring to FIG. 2, the user interface of the conventional anti-blinding device 2 includes a shade adjustment unit 6, a light detection sensitivity adjustment unit 7, and a time delay adjustment unit 8.

The shade adjustment unit 6 serves to adjust a shade value of the anti-blinding plate 5. Here, the shade value refers to a darkness degree of the anti-blinding plate 5. Accordingly, if the shade value of the anti-blinding plate 5 is adjusted by the shade adjustment unit 6, the light transmittance of the anti-blinding plate 5 is adjusted.

The light detection sensitivity adjustment unit 7 serves to adjust the light detection sensitivity of the anti-blinding device 2. The light detection sensitivity refers to a value indicating a degree to which the control circuit of the anti-blinding device 2 responds to an output signal of the photo-sensor unit 4. That is, if the light detection sensitivity level is high, the control circuit of the anti-blinding device 2 may respond to the output signal with low illumination intensity.

The time delay adjustment unit 8 serves to adjust the time delay of the anti-blinding device 2. If the time delay level is low, the control circuit of the anti-blinding device 2 rapidly switches the anti-blinding plate 5 from a dark state (opaque state) to a bright state (transparent state) when the photo-sensor unit 4 senses that a welding operation is completed. On the contrary, if the time delay level is high, the control circuit of the anti-blinding device 2 may take longer to be switched from the dark state to the bright state.

Typically, in industrial fields associated with the anti-blinding device, the shade value level is in a range of 5 to 13, the light detection sensitivity value level is in a range of 0 to 10, and the time delay value level is in a range of 0 to 10. The user interface of the conventional anti-blinding device 2 includes a power switch 9 used to turn power on or off, a battery 10 used to supply power, and a low voltage indicator 11 used to indicate a low voltage state of the device.

However, the above-described conventional anti-blinding device has a problem in that the anti-blinding plate does not provide effective indication and control of a screen display condition as well as a variation in light transmittance.

SUMMARY OF THE INVENTION

Therefore, the present invention has been made in view of the above problem, and it is an object of the present invention to provide a functional display type anti-blinding device, in which an anti-blinding plate, in the form of a variety of Liquid Crystal Displays (LCDs), is provided to assure effective indication and control of a screen display condition as well as a variation in light transmittance.

In accordance with an aspect of the present invention, the above and other objects can be accomplished by the provision of a functional display type anti-blinding device including an optical detecting unit to detect light emitted from a welding or cutting torch, an electromagnetic wave sensing unit to sense electromagnetic waves emitted from the welding or cutting torch, an electromagnetic wave detecting unit to compare a resonated signal received from the electromagnetic wave sensing unit with a variably set reference value, a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit, a light transmission control unit to control a variation in light transmittance of an anti-blinding plate based on an output signal of the control unit, and a display control unit to control a screen display condition of the anti-blinding plate based on an output signal of the control unit, wherein the anti-blinding plate includes a filter to selectively filter a predetermined wavelength of light, a polarizer to polarize the filtered light having passed through the filter, a shutter Liquid Crystal Display (LCD) arranged at a rear side of the polarizer, a light transmittance of which is varied based on the control of the light transmission control unit, a transparent dot-matrix LCD arranged at a rear side of the shutter LCD and serving to indicate the screen display condition based on the control of the display control unit, and a glass protector arranged at a rear side of the transparent dot-matrix LCD.

The shutter LCD may flicker several times when being initially turned on, so as to indicate that the anti-blinding plate is in an initial state and then, is turned off, and the transparent dot-matrix LCD may be turned on when the shutter LCD is turned off and serves to indicate the screen display condition.

The shutter LCD may be turned on when the transparent dot-matrix LCD is turned off and may serve to transmit light based on a preset light transmittance, so as to enable implementation of a welding operation.

Another polarizer may be further interposed between the shutter LCD and the transparent dot-matrix LCD, or between the transparent dot-matrix LCD and the glass protector.

In accordance with another aspect of the present invention, there is provided a functional display type anti-blinding device including an optical detecting unit to detect light emitted from a welding or cutting torch, an electromagnetic wave sensing unit to sense electromagnetic waves emitted from the welding or cutting torch, an electromagnetic wave detecting unit to compare a resonated signal received from the electromagnetic wave sensing unit with a variably set reference value, a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit, a light transmission control unit to control a variation in light transmittance of an anti-blinding plate based on an output signal of the control unit, and a display control unit to control a screen display condition of the anti-blinding plate based on an output signal of the control unit, wherein the anti-blinding plate includes a filter to selectively filter a predetermined wavelength of light, a polarizer to polarize the filtered light having passed through the filter, a first shutter Liquid Crystal Display (LCD) arranged at a rear side of the polarizer, a light transmittance of which is varied based on the control of the light transmission control unit, a second shutter LCD arranged at a rear side of the first shutter LCD, a light transmittance of which is varied based on the control of the light transmission control unit, a transparent dot-matrix LCD arranged at a rear side of the second shutter LCD and serving to indicate the screen display condition based on the control of the display control unit, and a glass protector arranged at a rear side of the transparent dot-matrix LCD.

The first and second shutter LCDs may flicker several times when being initially turned on, so as to indicate that the anti-blinding plate is in an initial state and then, may be turned off, and the transparent dot-matrix LCD may be turned on when the first and second shutter LCDs are turned off and serves to indicate the screen display condition.

The first and second shutter LCDs may be turned on when the transparent dot-matrix LCD is turned off and may serve to transmit light based on a preset light transmittance, so as to enable implementation of a welding operation.

Another polarizer may be further interposed between the first shutter LCD and the second shutter LCD, or between the transparent dot-matrix LCD and the glass protector.

In accordance with another aspect of the present invention, there is provided a functional display type anti-blinding device including an optical detecting unit to detect light emitted from a welding or cutting torch, an electromagnetic wave sensing unit to sense electromagnetic waves emitted from the welding or cutting torch, an electromagnetic wave detecting unit to compare a resonated signal received from the electromagnetic wave sensing unit with a variably set reference value, a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit, a light transmission control unit to control a variation in light transmittance of an anti-blinding plate based on an output signal of the control unit, and a display control unit to control a screen display condition of the anti-blinding plate based on an output signal of the control unit, wherein the anti-blinding plate includes a filter to selectively filter a predetermined wavelength of light, a polarizer to polarize the filtered light having passed through the filter, a first shutter Liquid Crystal Display (LCD) arranged at a rear side of the polarizer, a light transmittance of which is varied based on the control of the light transmission control unit, a second shutter LCD arranged at a rear side of the first shutter LCD, a light transmittance of which is varied based on the control of the light transmission control unit, a transparent segment LCD arranged at a rear side of the second shutter LCD and serving to indicate the screen display condition based on the control of the display control unit, and a glass protector arranged at a rear side of the transparent segment LCD.

The first and second shutter LCDs may flicker several times when being initially turned on, so as to indicate that the anti-blinding plate is in an initial state and then, may be turned off, and the transparent segment LCD may be turned on when the first and second shutter LCDs are turned off and serves to indicate the screen display condition.

The first and second shutter LCDs may be turned on when the transparent segment LCD is turned off and may serve to transmit light based on a preset light transmittance, so as to enable implementation of a welding operation.

Another polarizer may be further interposed between the first shutter LCD and the second shutter LCD, or between the transparent segment LCD and the glass protector.

In accordance with a further aspect of the present invention, there is provided a functional display type anti-blinding device including an optical detecting unit to detect light emitted from a welding or cutting torch, an electromagnetic wave sensing unit to sense electromagnetic waves emitted from the welding or cutting torch, an electromagnetic wave detecting unit to compare a resonated signal received from an electromagnetic wave sensing unit with a variably set reference value, a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit, a light transmission control unit to control a variation in light transmittance of an anti-blinding plate based on an output signal of the control unit, and a display control unit to control a screen display condition of the anti-blinding plate based on an output signal of the control unit, wherein the anti-blinding plate includes a filter to selectively filter a predetermined wavelength of light, a polarizer to polarize the filtered light having passed through the filter, a first shutter Liquid Crystal Display (LCD) arranged at a rear side of the polarizer, a light transmittance of which is varied based on the control of the light transmission control unit, a second shutter LCD arranged at a rear side of the first shutter LCD, a light transmittance of which is varied based on the control of the light transmission control unit, and a transparent segment dye LCD arranged at a rear side of the second shutter LCD and serving to indicate the screen display condition based on the control of the display control unit.

The first and second shutter LCDs may flicker several times when being initially turned on, so as to indicate that the anti-blinding plate is in an initial state and then, may be turned off, and the transparent segment dye LCD may be turned on when the first and second shutter LCDs are turned off and serves to indicate the screen display condition.

The first and second shutter LCDs may be turned on when the transparent segment dye LCD is turned off and may serve to transmit light based on a preset light transmittance, so as to enable implementation of a welding operation.

Another polarizer may be further interposed between the first shutter LCD and the second shutter LCD, or between the transparent segment dye LCD and the glass protector.

BRIEF DESCRIPTION OF THE DRAWINGS

The above and other objects, features and other advantages of the present invention will be more clearly understood from the following detailed description taken in conjunction with the accompanying drawings, in which.

DETAILED DESCRIPTION OF THE INVENTION

Figure 1:
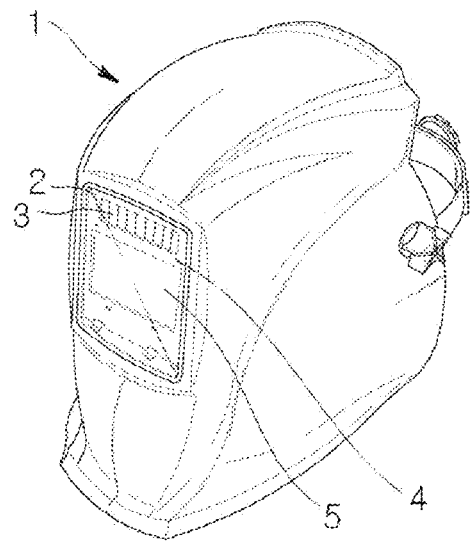
FIG. 1 is a perspective view illustrating a protective mask including a conventional anti-blinding device.
Figure 2:
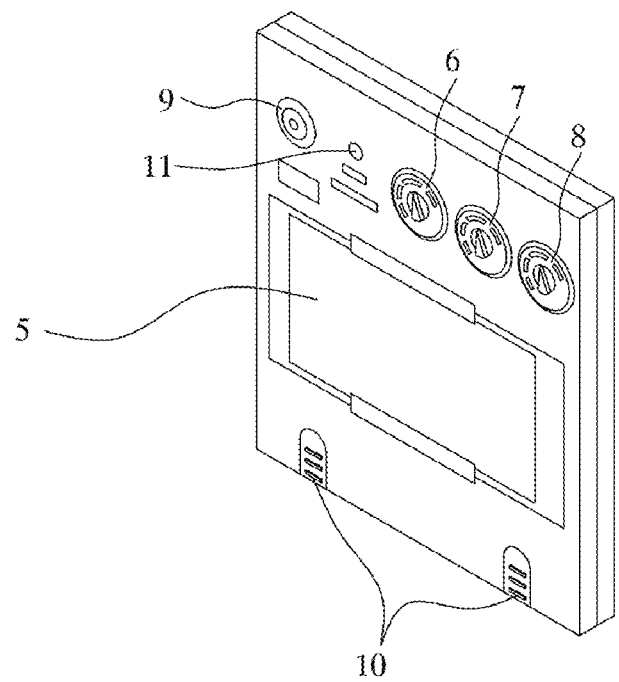
FIG. 2 is a view illustrating a user interface used to adjust the shade, light detection sensitivity, and time delay of the conventional anti-blinding device.

Hereinafter, exemplary embodiments of the present invention will be described in detail with reference to the accompanying drawings. The terms or words used in the specification and claims of the present invention are not interpreted using typical or dictionary limited meanings, and are construed as meanings and concepts conforming to the technical sprit of the present invention based on the principle that the inventors can appropriately define the concepts of the terms to explain the present invention in the best manner. Accordingly, it is to be understood that the detailed description, which will be disclosed along with the accompanying drawings, is intended to describe the exemplary embodiments of the present invention and is not intended to represent all technical ideas of the present invention. Therefore, it should be understood that various equivalents and modifications can exist which can replace the embodiments described in the time of the application.

Also, in the following description, it is noted that constituent elements of the present invention respectively corresponding to those of the previously described prior art are designated by the same reference numerals.

Figure 3:
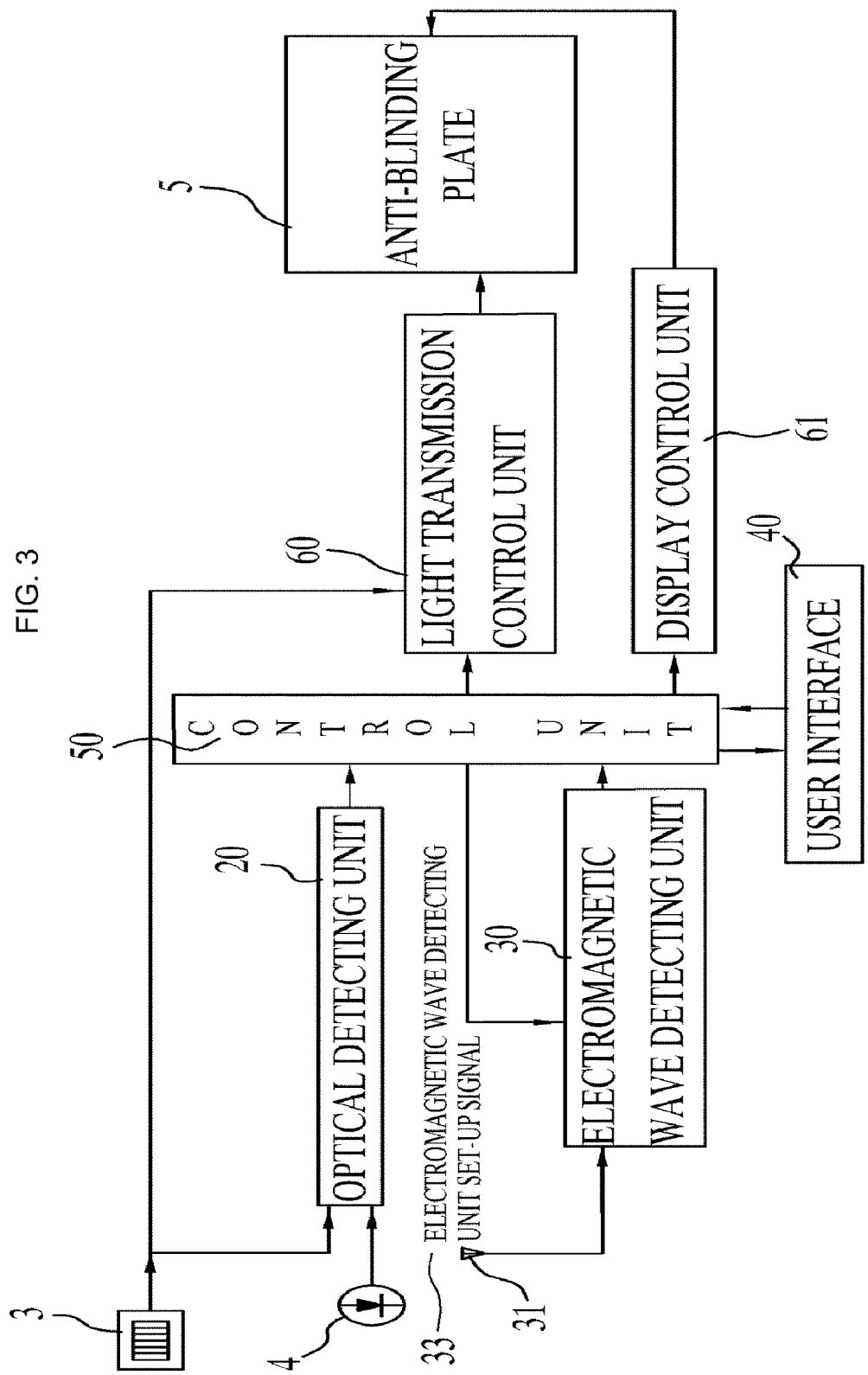
FIG. 3 is a block diagram illustrating a functional display type anti-blinding device according to the present invention.
Figure 4:
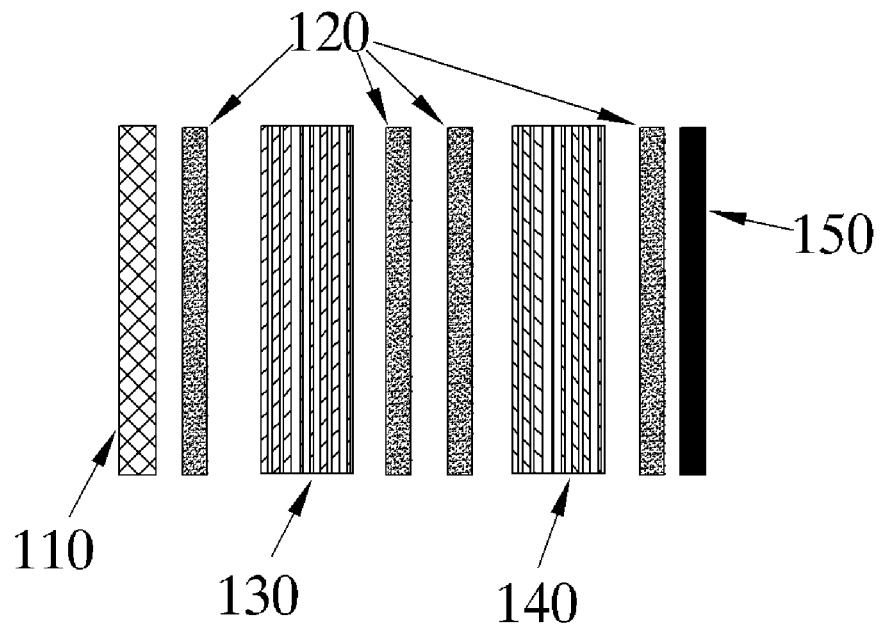
FIG. 4 is a view illustrating a configuration of an anti-blinding plate according to a first embodiment of the present invention.

FIG. 3 is a block diagram illustrating a functional display type anti-blinding device according to the present invention, and FIG. 4 is a view illustrating a configuration of an anti-blinding plate according to a first embodiment of the present invention.

As shown in FIG. 3, the anti-blinding device according to the present invention includes an anti-blinding plate 5, optical detecting unit 20, an electromagnetic wave detecting unit 30, an electromagnetic wave sensing unit 31, a user interface 40, a control unit 50, a light transmission control unit 60, and a display control unit 61.

The optical detecting unit 20 serves to detect light emitted from a welding or cutting torch. For this, the optical detecting unit 20 compares a signal received from a photo-sensor unit 4 with an output of a solar battery 3, thereby detecting a variation in the quantity of light.

The electromagnetic wave detecting unit 30 serves to detect electromagnetic waves emitted from the welding or cutting torch. For this, the electromagnetic wave detecting unit 30 compares a resonated and filtered signal output from the electromagnetic wave sensing unit 31, which senses the electromagnetic waves emitted from the welding or cutting torch, with a preset reference value, thereby detecting electromagnetic waves having a specific bandwidth.

The control unit 50 is adapted to apply an electromagnetic wave detecting unit start-up signal 33 to the electromagnetic wave detecting unit 30 and to monitor a variation in electromagnetic wave signal received from an output of the electromagnetic wave detecting unit 30, when optical detection is started by the optical detecting unit 20.

The light transmission control unit 60 serves to control a variation in the light transmittance of the anti-blinding plate 5 based on an output signal of the control unit 50.

The display control unit 61 serves to control a screen display condition of the anti-blinding plate 5 based on an output signal of the control unit 50.

For this, the anti-blinding plate 5, as shown in FIG. 4, includes: a filter 110 used to selectively filter a predetermined wavelength of light; a polarizer 120 used to polarize the filtered light having passed through the filter 110; a shutter Liquid Crystal Display (LCD) 130 arranged at a rear side of the polarizer 120, a light transmittance of which is varied based on the control of the light transmission control unit 60; a transparent dot-matrix LCD 140 arranged at a rear side of the shutter LCD 130 and used to indicate a screen display condition based on the control of the display control unit 61; and a glass protector 150 arranged at a rear side of the transparent dot-matrix LCD 140.

If the shutter LCD 130 is initially turned on, the shutter LCD 130 flickers several times, for example, two or three times to indicate that the anti-blinding plate 5 is in an initial state and then, is turned off. The transparent dot-matrix LCD 140 is turned on when the shutter LCD 130 is turned off and serves to indicate the screen display condition of the anti-blinding plate 5.

The shutter LCD 130 is turned on when the transparent dot-matrix LCD 140 is turned off and serves to transmit light based on a preset light transmittance, enabling the implementation of a welding operation.

In addition, another polarizer 120 may be further interposed between the shutter LCD 130 and the transparent dot-matrix LCD 140, or between the transparent dot-matrix LCD 140 and the glass protector 150.

Hereinafter, the first exemplary embodiment of the present invention based on the above-described configuration will be described in more detail.

First, the operator directly selects, operates, or adjusts the shade degree and the grind mode level by means of the user interface 40, so as to input the shade degree and the grind mode level to the control unit 50.

Next, the optical detecting unit 20 compares a signal received from the photo-sensor unit 4 with an output of the solar battery 3 to detect light emitted from the welding or cutting torch, thereby detecting a variation in the quantity of light.

Simultaneously, the electromagnetic wave detecting unit 30 detects electromagnetic waves emitted from the welding or cutting torch. Specifically, if the electromagnetic wave sensing unit 31 senses the electromagnetic waves emitted from the welding or cutting torch and inputs a corresponding resonated and filtered signal into the electromagnetic wave detecting unit 30, the electromagnetic wave detecting unit 30 compares the signal from the electromagnetic wave sensing unit 31 with a preset reference value, thereby detecting electromagnetic waves having a specific bandwidth.

Thereafter, the control unit 50 applies the electromagnetic wave detecting unit set-up signal 33 to the electromagnetic wave detecting unit 30, thereby monitoring a variation in an electromagnetic wave signal received from the output of the electromagnetic wave detecting unit 30, when optical detection is started by the optical detecting unit 20.

Accordingly, the light transmission control unit 60 controls a variation in the light transmittance of the anti-blinding plate 5 based on the output signal of the control unit 5, thereby controlling the light transmittance to a predetermined value or less.

The display control unit 61 controls the screen display condition of the anti-blinding plate 5 based on the output signal from the control unit 50.

In this case, the filter 110 of the anti-blinding plate 5 selectively filters a predetermined wavelength of light, and the polarizer 120 polarizes the filtered light having passed through the filter 110.

The light transmittance of the shutter LCD 130 arranged at the rear side of the polarizer 120 is varied under the control of the light transmission control unit 60. If the shutter LCD 130 is initially turned on, the shutter LCD 130 flickers several times, for example, two or three times to indicate that the anti-blinding plate 5 is in an initial state and then, is turned off.

Thereafter, the transparent dot-matrix LCD 140, arranged at the rear side of the shutter LCD 130, indicates the screen display condition under the control of the display control unit 61. For this, the transparent dot-matrix LCD 140 is turned on when the shutter LCD 130 is turned off.

The shutter LCD 130 is turned on when the transparent dot-matrix LCD 140 is turned off, thereby serving to transmit light based on a preset light transmittance. In this way, the implementation of a welding operation is possible.

The transparent dot-matrix LCD 140 may indicate, at a front surface thereof, a current time, everyday working time, accumulated working time, temperature and humidity of a working place in alphanumeric form.

Accordingly, when the anti-blinding device is switched to an OFF-state and is stopped in operation, the anti-blinding plate 5 is kept transparent to allow the operator to easily view outside. In the off-state, the anti-blinding device is switched to an On-state by the light transmission control unit 60, so as to be operated in an initial screen standby mode. That is, the shutter LCD 130 flickers two or three times to indicate that the anti-blinding plate 5 is in an initial state. The transparent dot-matrix LCD 140 is turned on simultaneously with the shutter LCD 130 being turned off, to indicate various preset operating conditions (e.g., the shade level, sensitivity, and time delay) on a welding mask. Here, the operating conditions are set up by the user interface 40. In this case, a transparent display part of the welding mask is indicated as a negative state.

Thereafter, the shutter LCD 130 is turned on after the operator confirms the above conditions and simultaneously, the transparent dot-matrix LCD 140 is turned off, allowing the operator to carry out a normal welding operation.

Figure 5:
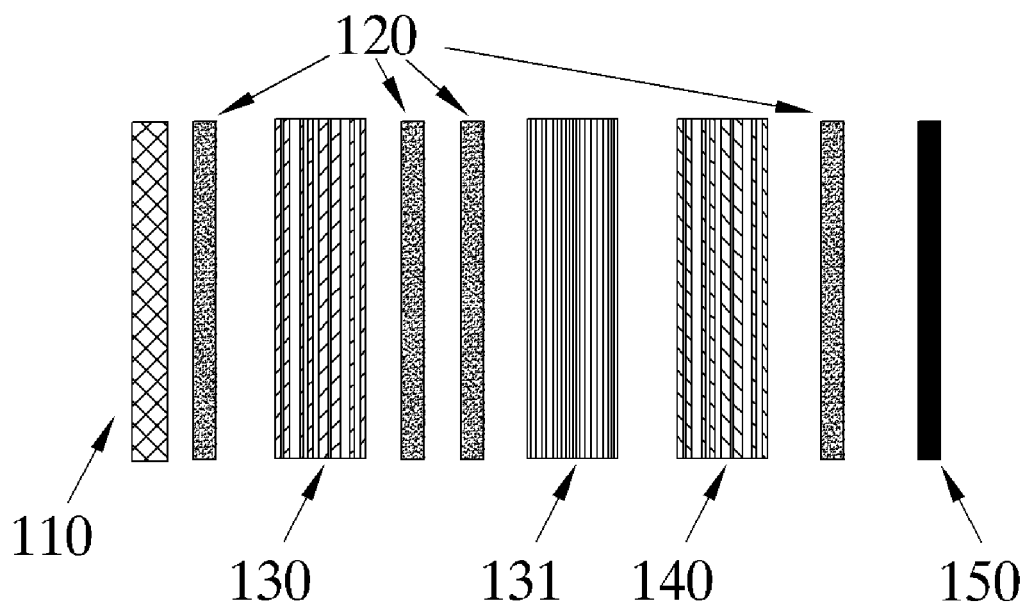
FIG. 5 is a view illustrating a configuration of an anti-blinding plate according to a second embodiment of the present invention.

FIG. 5 is a view illustrating a configuration of an anti-blinding plate according to a second embodiment of the present invention.

In the second embodiment of the present invention, the anti-blinding device includes the anti-blinding plate 5, the optical detecting unit 20, the electromagnetic wave detecting unit 30, the electromagnetic wave sensing unit 31, the user interface 40, the control unit 50, the light transmission control unit 60, and the display control unit 61. The operation of the anti-blinding device according to the second embodiment is identical to that of the above-described first embodiment.

Exceptionally, the anti-blinding plate 5 according to the second embodiment includes: the filter 110 used to selectively filter a predetermined wavelength of light; the polarizer 120 used to polarize the filtered light having passed through the filter 110; a first shutter LCD 130 arranged at the rear side of the polarizer 120, a light transmittance of which is varied based on the control of the light transmission control unit 60; a second shutter LCD 131 arranged at a rear side of the first shutter LCD 130, a light transmittance of which is varied based on the control of the light transmission control unit 60; the transparent dot-matrix LCD 140 arranged at a rear side of the second shutter LCD 131 and used to indicate the screen display condition based on the control of the display control unit 61; and the glass protector 150 arranged at the rear side of the transparent dot-matrix LCD 140.

If the first and second shutter LCDs 130 and 131 are initially turned on, both the shutter LCDs 130 and 131 flicker several times to indicate that the anti-blinding plate 5 is in an initial state and then, are turned off. The transparent dot-matrix LCD 140 is turned on when the first and second shutter LCDs 130 and 131 are turned off, to indicate the screen display condition of the anti-blinding plate 5.

The first and second shutter LCDs 130 and 131 are turned on when the transparent dot-matrix LCD 140 is turned off, to transmit light based on a preset light transmittance, thereby enabling the implementation of a welding operation.

In addition, another polarizer 120 may be interposed between the first shutter LCD 130 and the second shutter LCD 131, or between the transparent dot-matrix LCD 140 and the glass protector 150.

Figure 6:
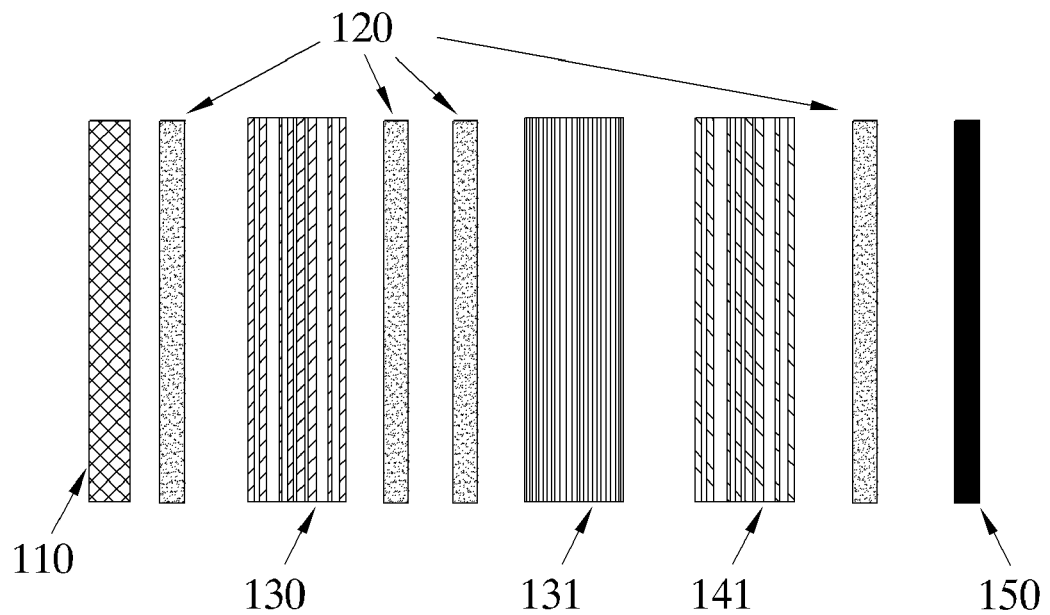
FIG. 6 is a view illustrating a configuration of an anti-blinding plate according to a third embodiment of the present invention.

FIG. 6 is a view illustrating a configuration of an anti-blinding plate according to a third embodiment of the present invention.

In the third embodiment of the present invention, the anti-blinding device includes the anti-blinding plate 5, the optical detecting unit 20, the electromagnetic wave detecting unit 30, the electromagnetic wave sensing unit 31, the user interface 40, the control unit 50, the light transmission control unit 60, and the display control unit 61. The operation of the anti-blinding device according to the third embodiment is identical to that of the above-described first embodiment.

Exceptionally, the anti-blinding plate 5 according to the third embodiment includes: the filter 110 used to selectively filter a predetermined wavelength of light; the polarizer 120 used to polarize the filtered light having passed through the filter 110; the first shutter LCD 130 arranged at the rear side of the polarizer 120, the light transmittance of which is varied based on the control of the light transmission control unit 60; the second shutter LCD 131 arranged at the rear side of the first shutter LCD 130, a light transmittance of which is varied based on the control of the light transmission control unit 60; a transparent segment LCD 141 arranged at a rear side of the second shutter LCD 131 and used to indicate the screen display condition based on the control of the display control unit 61; and the glass protector 150 arranged at a rear side of the transparent segment LCD 141.

If the first and second shutter LCDs 130 and 131 are initially turned on, both the shutter LCDs 130 and 131 flicker several times, for example, two or three times to indicate that the anti-blinding plate 5 is in an initial state and then, are turned off.

The transparent segment LCD 141 is turned on when the first and second shutter LCDs 130 and 131 are turned off, to indicate the screen display condition of the anti-blinding plate 5.

The first and second shutter LCDs 130 and 131 are turned on when the transparent segment LCD 141 is turned off, to transmit light based on a preset light transmittance, thereby enabling the implementation of a welding operation.

In addition, another polarizer 120 may be interposed between the first shutter LCD 130 and the second shutter LCD 131, or between the transparent segment LCD 141 and the glass protector 150.

Figure 7:
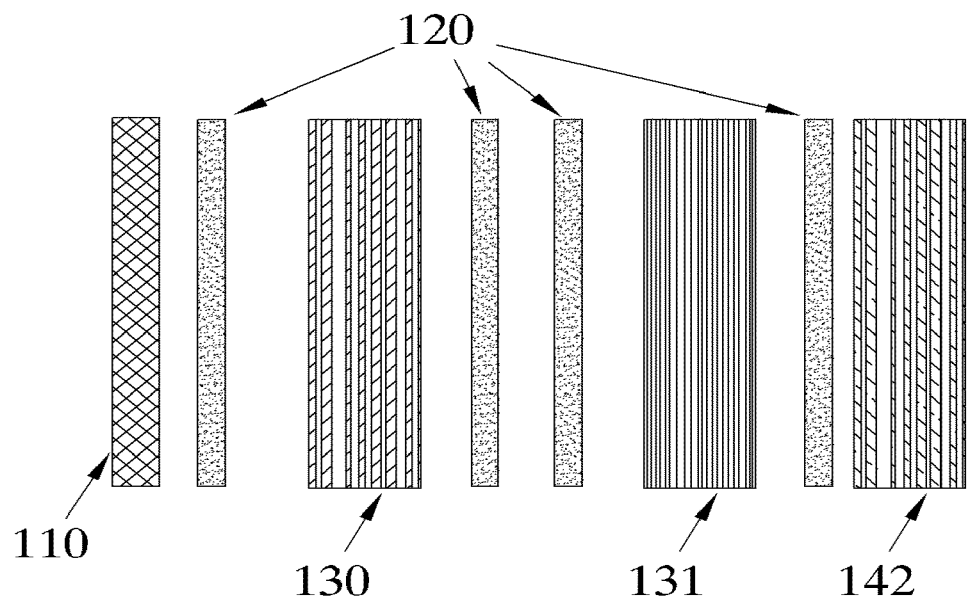
FIG. 7 is a view illustrating a configuration of an anti-blinding plate according to a fourth embodiment of the present invention.

FIG. 7 is a view illustrating a configuration of an anti-blinding plate according to a fourth embodiment of the present invention.

In the fourth embodiment of the present invention, the anti-blinding device includes the anti-blinding plate 5, the optical detecting unit 20, the electromagnetic wave detecting unit 30, the electromagnetic wave sensing unit 31, the user interface 40, the control unit 50, the light transmission control unit 60, and the display control unit 61. The operation of the anti-blinding device according to the fourth embodiment is identical to that of the above-described first embodiment.

Exceptionally, the anti-blinding plate 5 according to the fourth embodiment includes: the filter 110 used to selectively filter a predetermined wavelength of light; the polarizer 120 used to polarize the filtered light having passed through the filter 110; the first shutter LCD 130 arranged at the rear side of the polarizer 120, a light transmittance of which is varied based on the control of the light transmission control unit 60; the second shutter LCD 131 arranged at the rear side of the first shutter LCD 130, a light transmittance of which is varied based on the control of the light transmission control unit 60; and a transparent segment dye LCD 142 arranged at the rear side of the second shutter LCD 131 and used to indicate the screen display condition based on the control of the display control unit 61.

If the first and second shutter LCDs 130 and 131 are initially turned on, both the shutter LCDs 130 and 131 flicker several times, for example, two or three times to indicate that the anti-blinding plate 5 is in an initial state and then, are turned off.

The transparent segment dye LCD 142 is turned on when the first and second shutter LCDs 130 and 131 are turned off, to indicate the screen display condition of the anti-blinding plate 5.

The first and second shutter LCDs 130 and 131 are turned on when the transparent segment dye LCD 142 is turned off, to transmit light based on a preset light transmittance, thereby enabling the implementation of a welding operation.

In addition, another polarizer 120 may be interposed between the first shutter LCD 130 and the second shutter LCD 131, or between the second shutter LCD 131 and the transparent segment dye LCD 142.

Figure 8:
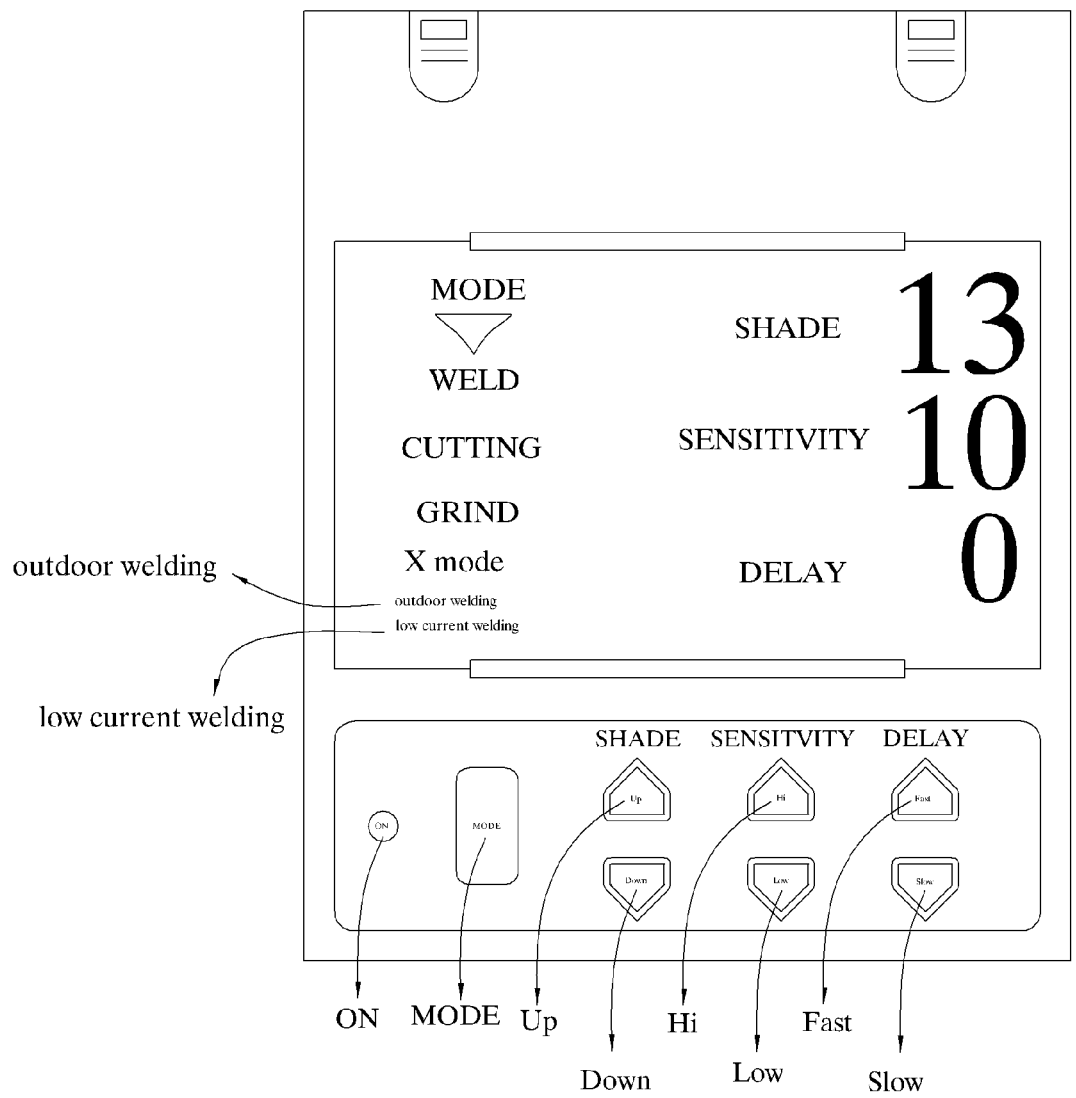
FIGS. 8 and 9 are views illustrating a screen of the functional display type anti-blinding device according to the present invention.
Figure 9:
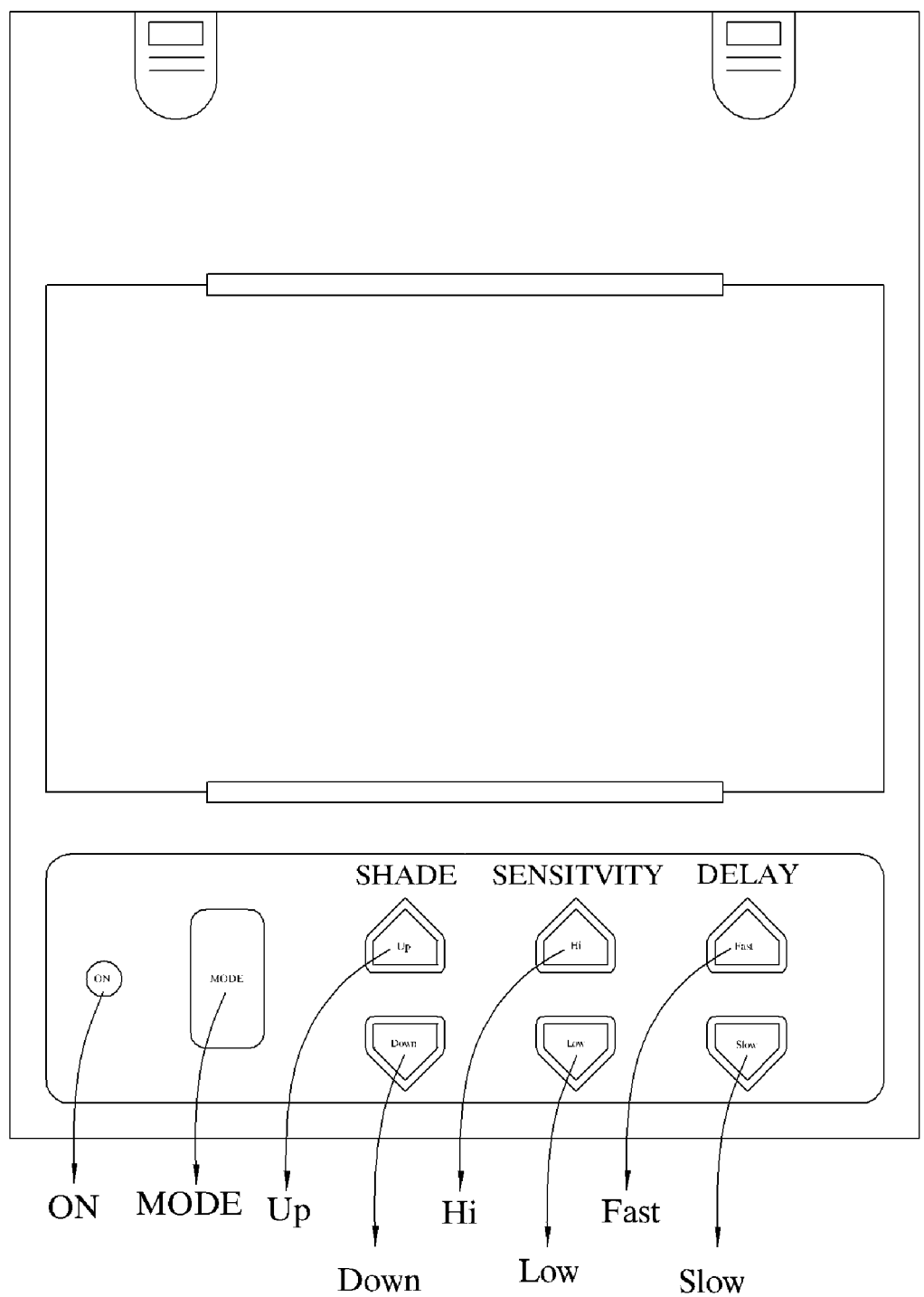

FIGS. 8 and 9 are views illustrating a screen of the functional display type anti-blinding device according to the present invention, FIG. 8 illustrating a state in which an information display LCD image is in an On-state to be displayed, and FIG. 9 illustrating a state in which the information display LCD image is in an Off-state so as not to be displayed.

In the present invention, the anti-blinding device further includes a touch sensor input unit, which serves to recognize a shade degree and a grind mode level by direct selective operation or adjustment of the operator in a digital contact signal and to input the shade degree and the grind mode level to the control unit 50.

The touch sensor input unit is provided on the anti-blinding plate 5. Specifically, the touch sensor input unit may include a Printed Circuit Board (PCB) (not shown) formed by mounting or printing a conductive metal or a conductive material at a predetermined interval, and an electrode plate (not shown) formed on the PCB and serving to send a contact signal to the control unit 50 in response to static electricity of a human body when a finger of the human body approaches or touches the electrode plate.

As apparent from the above description, the present invention provides a functional display type anti-blinding device in which an anti-blinding plate, in the form of a variety of Liquid Crystal Displays (LCDs), is provided. The anti-blinding device has the effects of assuring effective indication and control of a screen display condition as well as a variation in light transmittance.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A functional display type anti-blinding device comprising:
an optical detecting unit to detect light emitted from a welding or cutting torch;
an electromagnetic wave sensing unit to sense electromagnetic waves emitted from the welding or cutting torch;
an electromagnetic wave detecting unit to compare a resonated signal received from the electromagnetic wave sensing unit with a variably set reference value;
a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit;
a light transmission control unit to control a variation in light transmittance of an anti-blinding plate based on an output signal of the control unit; and
a display control unit to control a screen display condition of the anti-blinding plate based on an output signal of the control unit,
wherein the anti-blinding plate includes:
a filter to selectively filter a predetermined wavelength of light;
a polarizer to polarize the filtered light having passed through the filter;
a shutter Liquid Crystal Display (LCD) arranged at a rear side of the polarizer, a light transmittance of which is varied based on the control of the light transmission control unit;
a transparent dot-matrix LCD arranged at a rear side of the shutter LCD and serving to indicate the screen display condition based on the control of the display control unit; and
a glass protector arranged at a rear side of the transparent dot-matrix LCD.

2. The device according to claim 1, wherein:
the shutter LCD flickers several times when being initially turned on, so as to indicate that the anti-blinding plate is in an initial state and then, is turned off; and
the transparent dot-matrix LCD is turned on when the shutter LCD is turned off and serves to indicate the screen display condition.

3. The device according to claim 2, wherein the shutter LCD is turned on when the transparent dot-matrix LCD is turned off and serves to transmit light based on a preset light transmittance, so as to enable implementation of a welding operation.

4. The device according to claim 1, wherein another polarizer is further interposed between the shutter LCD and the transparent dot-matrix LCD, or between the transparent dot-matrix LCD and the glass protector.

5. The device according to claim 1, further comprising:
a touch sensor input unit to recognize a shade degree and a grind mode level by direct selective operation or adjustment of an operator in a digital contact signal and to input the shade degree and the grind mode level to the control unit.

6. The device according to claim 5, wherein the touch sensor input unit is formed on the anti-blinding plate.

7. A functional display type anti-blinding device comprising:
an optical detecting unit to detect light emitted from a welding or cutting torch;
an electromagnetic wave sensing unit to sense electromagnetic waves emitted from the welding or cutting torch;
an electromagnetic wave detecting unit to compare a resonated signal received from the electromagnetic wave sensing unit with a variably set reference value;
a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit;
a light transmission control unit to control a variation in light transmittance of an anti-blinding plate based on an output signal of the control unit; and
a display control unit to control a screen display condition of the anti-blinding plate based on an output signal of the control unit,
wherein the anti-blinding plate includes:
a filter to selectively filter a predetermined wavelength of light;
a polarizer to polarize the filtered light having passed through the filter;
a first shutter Liquid Crystal Display (LCD) arranged at a rear side of the polarizer, a light transmittance of which is varied based on the control of the light transmission control unit;
a second shutter LCD arranged at a rear side of the first shutter LCD, a light transmittance of which is varied based on the control of the light transmission control unit;
a transparent dot-matrix LCD arranged at a rear side of the second shutter LCD and serving to indicate the screen display condition based on the control of the display control unit; and
a glass protector arranged at a rear side of the transparent dot-matrix LCD.

8. The device according to claim 7, wherein:
the first and second shutter LCDs flicker several times when being initially turned on, so as to indicate that the anti-blinding plate is in an initial state and then, are turned off; and
the transparent dot-matrix LCD is turned on when the first and second shutter LCDs are turned off, and serves to indicate the screen display condition.

9. The device according to claim 8, wherein the first and second shutter LCDs are turned on when the transparent dot-matrix LCD is turned off, and serve to transmit light based on a preset light transmittance, so as to enable implementation of a welding operation.

10. The device according to claim 7, wherein another polarizer is further interposed between the first shutter LCD and the second shutter LCD, or between the transparent dot-matrix LCD and the glass protector.

11. The device according to claim 7, further comprising:
a touch sensor input unit to recognize a shade degree and a grind mode level by direct selective operation or adjustment of an operator in a digital contact signal and to input the shade degree and the grind mode level to the control unit.

12. The device according to claim 11, wherein the touch sensor input unit is formed on the anti-blinding plate.

13. A functional display type anti-blinding device comprising:
an optical detecting unit to detect light emitted from a welding or cutting torch;
an electromagnetic wave sensing unit to sense electromagnetic waves emitted from the welding or cutting torch;
an electromagnetic wave detecting unit to compare a resonated signal received from the electromagnetic wave sensing unit with a variably set reference value;
a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit;
a light transmission control unit to control a variation in light transmittance of an anti-blinding plate based on an output signal of the control unit; and
a display control unit to control a screen display condition of the anti-blinding plate based on an output signal of the control unit,
wherein the anti-blinding plate includes:
a filter to selectively filter a predetermined wavelength of light;
a polarizer to polarize the filtered light having passed through the filter;
a first shutter Liquid Crystal Display (LCD) arranged at a rear side of the polarizer, a light transmittance of which is varied based on the control of the light transmission control unit;
a second shutter LCD arranged at a rear side of the first shutter LCD, a light transmittance of which is varied based on the control of the light transmission control unit;
a transparent segment LCD arranged at a rear side of the second shutter LCD and serving to indicate the screen display condition based on the control of the display control unit; and
a glass protector arranged at a rear side of the transparent segment LCD.

14. The device according to claim 13, wherein:
the first and second shutter LCDs flicker several times when being initially turned on, so as to indicate that the anti-blinding plate is in an initial state and then, are turned off; and
the transparent segment LCD is turned on when the first and second shutter LCDs are turned off, and serves to indicate the screen display condition.

15. The device according to claim 14, wherein the first and second shutter LCDs are turned on when the transparent segment LCD is turned off, and serve to transmit light based on a preset light transmittance, so as to enable implementation of a welding operation.

16. The device according to claim 13, wherein another polarizer is further interposed between the first shutter LCD and the second shutter LCD, or between the transparent segment LCD and the glass protector.

17. The device according to claim 13, further comprising:
a touch sensor input unit to recognize a shade degree and a grind mode level by direct selective operation or adjustment of an operator in a digital contact signal and to input the shade degree and the grind mode level to the control unit.

18. The device according to claim 17, wherein the touch sensor input unit is formed on the anti-blinding plate.

19. A functional display type anti-blinding device comprising:
an optical detecting unit to detect light emitted from a welding or cutting torch;
an electromagnetic wave sensing unit to sense electromagnetic waves emitted from the welding or cutting torch;
an electromagnetic wave detecting unit to compare a resonated signal received from an electromagnetic wave sensing unit with a variably set reference value;
a control unit to apply an electromagnetic wave detecting unit start-up signal to the electromagnetic wave detecting unit and to monitor a variation in an electromagnetic wave signal received from an output of the electromagnetic wave detecting unit, when optical detection is started by the optical detecting unit;
a light transmission control unit to control a variation in light transmittance of an anti-blinding plate based on an output signal of the control unit; and
a display control unit to control a screen display condition of the anti-blinding plate based on an output signal of the control unit,
wherein the anti-blinding plate includes:
a filter to selectively filter a predetermined wavelength of light;
a polarizer to polarize the filtered light having passed through the filter;
a first shutter Liquid Crystal Display (LCD) arranged at a rear side of the polarizer, a light transmittance of which is varied based on the control of the light transmission control unit;
a second shutter LCD arranged at a rear side of the first shutter LCD, a light transmittance of which is varied based on the control of the light transmission control unit; and
a transparent segment dye LCD arranged at a rear side of the second shutter LCD and serving to indicate the screen display condition based on the control of the display control unit.

20. The device according to claim 19, wherein:
the first and second shutter LCDs flicker several times when being initially turned on, so as to indicate that the anti-blinding plate is in an initial state and then, are turned off; and
the transparent segment dye LCD is turned on when the first and second shutter LCDs are turned off, and serves to indicate the screen display condition.

21. The device according to claim 20, wherein the first and second shutter LCDs are turned on when the transparent segment dye LCD is turned off, and serve to transmit light based on a preset light transmittance, so as to enable implementation of a welding operation.

22. The device according to claim 19, wherein another polarizer is further interposed between the first shutter LCD and the second shutter LCD, or between the transparent segment dye LCD and the glass protector.

23. The device according to claim 19, further comprising:
a touch sensor input unit to recognize a shade degree and a grind mode level by direct selective operation or adjustment of an operator in a digital contact signal and to input the shade degree and the grind mode level to the control unit.

24. The device according to claim 23, wherein the touch sensor input unit is formed on the anti-blinding plate.

* * * * *